(12) United States Patent
Blum

(10) Patent No.: US 12,078,726 B2
(45) Date of Patent: Sep. 3, 2024

(54) METHOD OF DETECTING HYDROCARBON BUBBLES USING AIRBORNE LIGHT DETECTION AND RANGING

(71) Applicant: ExxonMobil Technology and Engineering Company, Spring, TX (US)

(72) Inventor: John Blum, Houston, TX (US)

(73) Assignee: ExxonMobil Technology and Engineering Company, Spring, TX (US)

( * ) Notice: Subject to any disclaimer, the term of this patent is extended or adjusted under 35 U.S.C. 154(b) by 685 days.

(21) Appl. No.: 16/948,707

(22) Filed: Sep. 29, 2020

(65) Prior Publication Data

US 2021/0116566 A1 Apr. 22, 2021

Related U.S. Application Data

(60) Provisional application No. 62/924,253, filed on Oct. 22, 2019.

(51) Int. Cl.
*G01S 17/88* (2006.01)
*G01N 33/18* (2006.01)

(52) U.S. Cl.
CPC .......... *G01S 17/88* (2013.01); *G01N 33/1833* (2013.01)

(58) Field of Classification Search
CPC .............................. G01S 17/88; G01N 33/1833
See application file for complete search history.

(56) References Cited

U.S. PATENT DOCUMENTS

| 5,257,085 | A | * | 10/1993 | Ulich | G01J 3/2823 |
| | | | | | 356/73 |
| 9,146,225 | B2 | | 9/2015 | Pottorf et al. | |
| 9,453,828 | B2 | | 9/2016 | Corbett et al. | |
| 9,612,231 | B2 | | 4/2017 | Pottorf et al. | |
| 9,638,828 | B2 | | 5/2017 | Levien et al. | |
| 9,829,602 | B2 | | 11/2017 | Bond et al. | |
| 9,891,331 | B2 | | 2/2018 | Hornbostel et al. | |

FOREIGN PATENT DOCUMENTS

NO 20160882 A1 * 11/2017 ............. G06F 21/62

OTHER PUBLICATIONS

Carter, Jamie et al., "Lidar 101: An Introduction to Lidar Technology, Data, and Applications", Nov. 2012, NOAA Coastal Services Center (Year: 2012).*

(Continued)

*Primary Examiner* — Luke D Ratcliffe
(74) *Attorney, Agent, or Firm* — Lempia Summerfield Katz LLC

(57) ABSTRACT

Detection of hydrocarbon bubbles in water using Light Detection and Ranging (LIDAR) to survey shallow water environments for the detection of surface hydrocarbon bubbles therein using LIDAR for the purposes of hydrocarbon exploration and/or brownfield remediation. Embodiments include a method of deploying an airborne LIDAR system configured to detect surface hydrocarbon bubbles in a shallow water environment, the LIDAR system accounting for a bubble volume scattering coefficient; and surveying, using the LIDAR system, the shallow water environment to detect surface hydrocarbon bubbles therein.

13 Claims, 6 Drawing Sheets

(56) References Cited

OTHER PUBLICATIONS

Howell, John et al., "Distribution of discontinuous mudstone beds within wave-dominated shallow-marine deposits: Star Point and Blackhawk Formations, Eastern Utah, USA", Jul. 2014, AAPG Bulletin, vol. 98, No. 7, pp. 1401-1429 (Year: 2014).*

Krupnik, Diana et al., "Study of Upper Albian rudist buildups in the Edwards Formation using ground-based hyperspectral imaging and terrestrial laser scanning", Sep. 30, 2016, Elsevier B.V., Sedimentary Geology 345, pp. 154-167 (Year: 2016).*

Spence, Guy et al., "Lidar outcrop analogues of a naturally fractured carbonate reservoir; influences of stratigraphic heterogeneity and surfaces; a sequence stratigraphic framework; Eocene, Thebes Formation, west central Sinai, Egypt", Oct. 2011, Geological Society of America, Abstract (Year: 2011).*

Blake, Brittney et al., "Fracture Heterogeneity in the Natih E Formation, Jebel Madar, Oman", 2009, Annual AAPG Convention, Abstract (Year: 2009).*

Brake, Daniel et al., "New Airborne Remote Sensing Service Enhances Pipeline Integrity Assessment", Jun. 2004, Pipeline and Gas Journal, pp. 28-30 (Year: 2004).*

Grishkanich, A. S., et al. "Lidar for monitoring methane emission in Siberian permafrost." High Energy/Average Power Lasers and Intense Beam Applications IX. vol. 9729. SPIE, 2016. (Year: 2016).*

Churnside, J. H. (2010) "Lidar signature from bubbles in the sea," Opt. Express 18, pp. 8294-8299.

Roddewig et al. (2017) "Dual-polarization airborne lidar for freshwater fisheries management and research," Opt. Eng. vol. 56, No. 3, 031221, doi: 10.1117/1.OE.56.3.031221, 12 pgs.

Roddewig et al. (2017) "Airborne lidar detection of an underwater thermal vent", J. Appl. Remote Sens., vol. 11, No. 3, 036014, doi: 10.1117/1.JRS.11.036014, 8 pgs.

Roddewig et al. (2018) "Airborne lidar detection and mapping of invasive lake trout in Yellowstone Lake", Appl. Opt. 57, 7 pgs.

* cited by examiner

METHOD OF DETECTING HYDROCARBON BUBBLES USING AIRBORNE LIGHT DETECTION AND RANGING

CROSS REFERENCE TO RELATED APPLICATION

This application claims the priority of U.S. Provisional Application Ser. No. 62/924,253, filed Oct. 22, 2019, the disclosure of which is incorporated herein by reference in its entirety.

FIELD

The present disclosure relates to the detection of hydrocarbon bubbles in water using Light Detection and Ranging (LIDAR).

BACKGROUND

Surface (i.e., shallow water) geochemical prospecting for hydrocarbon sources may be vital for locating undiscovered sources of desirable hydrocarbon reserves, as well as locating undiscovered sources of potential hydrocarbon contamination. Hydrocarbon exploration may be facilitated by detecting hydrocarbon sources that are optimal or otherwise suitable for downstream oil and gas applications, such as the production of energy and consumer petroleum-based goods. Conversely, certain environments are required to meet strict federal, state, and local standards with respect to the absence of hydrocarbons, such as urban brownfield environments. Detection of surface hydrocarbon in such environments may facilitate compliance with the required standards and any necessary remediation efforts.

LIDAR is a remote surveying and sensing technique that utilizes pulsed laser light to measure distance and identify targets. The pulsed laser light is reflected off the target and based on the laser return time and wavelength, the target's location can be identified. LIDAR is used in terrestrial, mobile, and airborne applications. LIDAR advantageously allows quick and accurate data collection with relatively high accuracy, is not affected by light variations and thus can be used at any time of day or night, can be integrated with other sources of data for enhancing analysis, and is relatively inexpensive. Recent advancements in LIDAR techniques have been employed experimentally or theoretically to map the Earth's surface and locate various flora and fauna. For example, LIDAR has been used to detect lake thermal vents and fish schools in shallow mountain lakes. It has further been theorized that LIDAR may be used to detect bubbles in the sea produced by breaking waves.

Therefore, it would be desirable to have a method of using LIDAR to detect surface hydrocarbon bubbles in water for the purposes of hydrocarbon exploration and brownfield remediation.

BRIEF DESCRIPTION OF THE DRAWINGS

The following figures are included to illustrate certain aspects of the embodiments, and should not be viewed as exclusive embodiments. The subject matter disclosed is capable of considerable modifications, alterations, combinations, and equivalents in form and function, as will occur to those skilled in the art and having the benefit of this disclosure.

DETAILED DESCRIPTION

Figure 1:
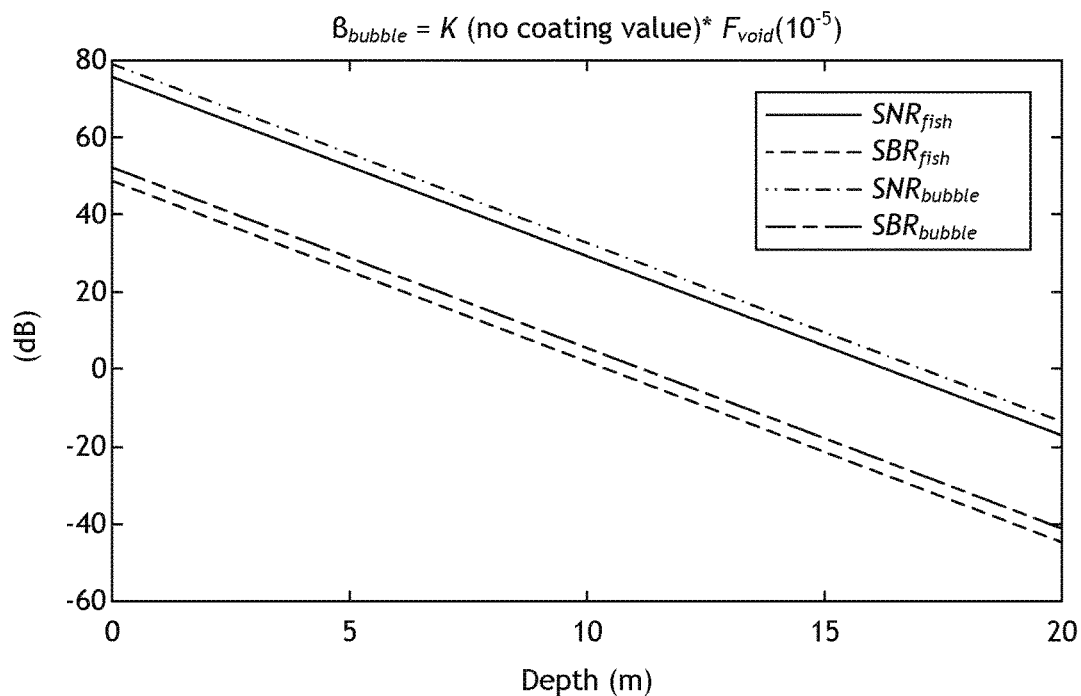
FIG. 1 is a plot showing signal-to-noise ratio and signal-to-background ratio for volume scattering coefficient $\beta_{bubble}$, with no coating and a void fraction of bubbles beneath the LIDAR footprint of $10^{-5}$, compared to $\beta_{fish}$, as described herein as a similar application to detecting fish via LIDAR.
Figure 2:
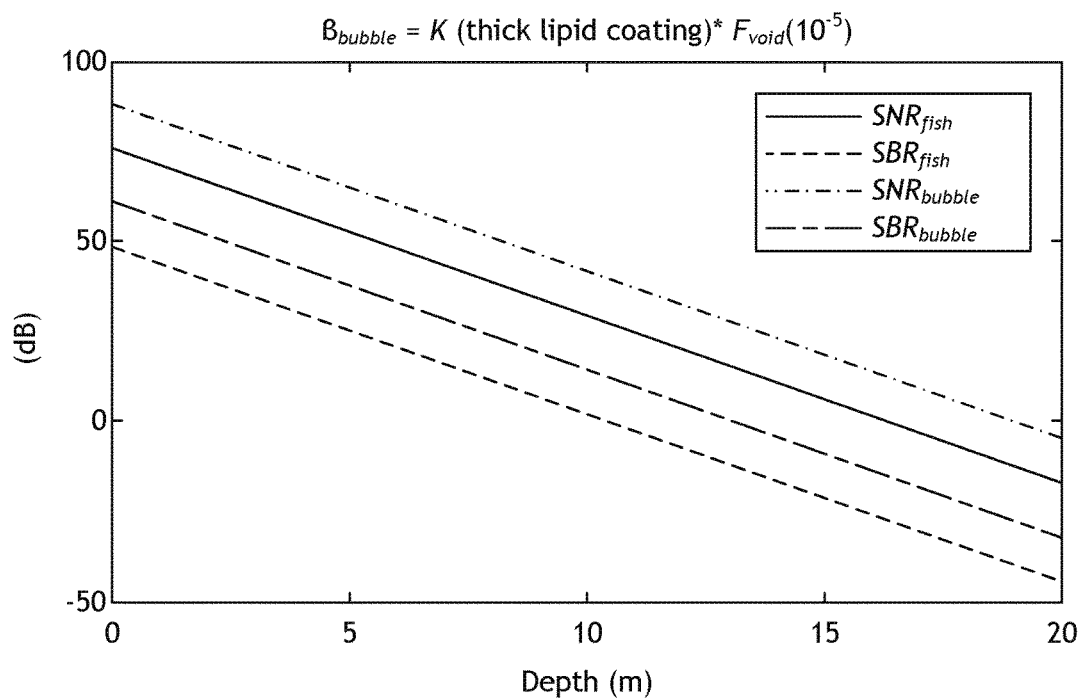
FIG. 2 is a plot showing signal-to-noise ratio and signal-to-background ratio for volume scattering coefficient $\beta_{bubble}$, with a thick lipid coating and a void fraction of bubbles beneath the LIDAR footprint of $10^{-5}$, compared to $\beta_{fish}$, as described herein.
Figure 3:
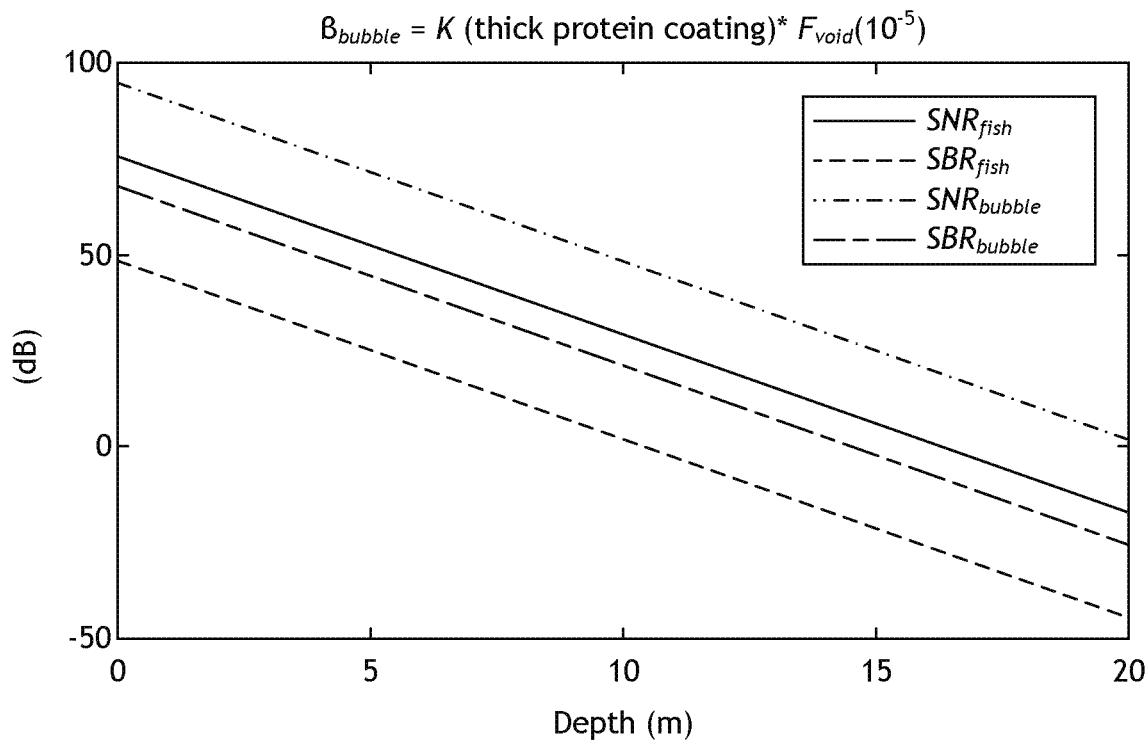
FIG. 3 is a plot showing signal-to-noise ratio and signal-to-background ratio for volume scattering coefficient $\beta_{bubble}$, with a thick protein coating and a void fraction of bubbles beneath the LIDAR footprint of $10^{-5}$, compared to $\beta_{fish}$, as described herein.
Figure 4:
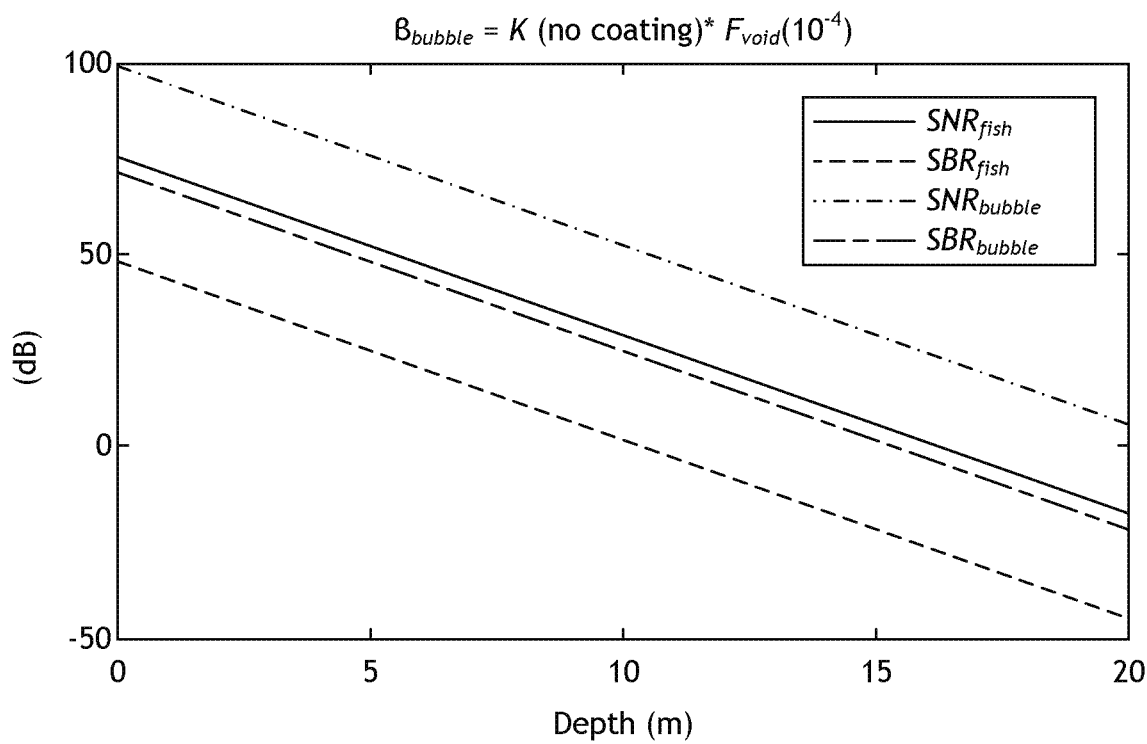
FIG. 4 is a plot showing signal-to-noise ratio and signal-to-background ratio for volume scattering coefficient $\beta_{bubble}$, with no coating and a void fraction of bubbles beneath the LIDAR footprint of $10^{-4}$, compared to $P_{fish}$, as described herein.
Figure 5:
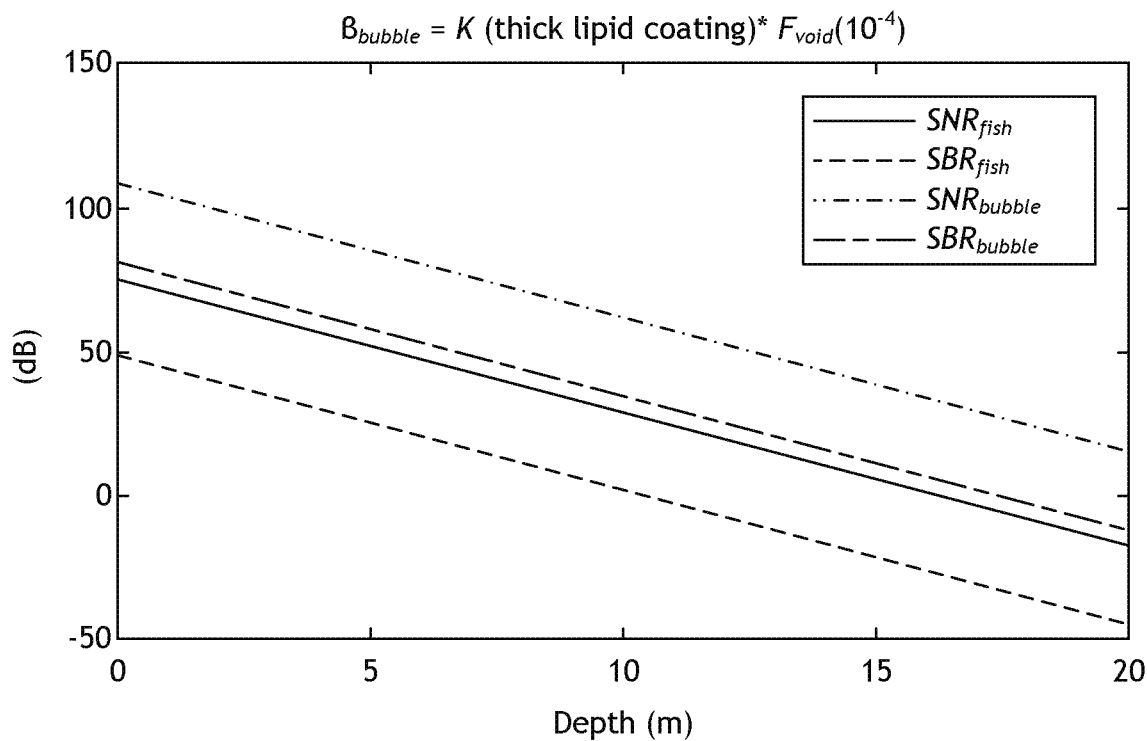
FIG. 5 is a plot showing signal-to-noise ratio and signal-to-background ratio for volume scattering coefficient $\beta_{bubble}$, with a thick lipid coating and a void fraction of bubbles beneath the LIDAR footprint of $10^{-4}$, compared to $\beta_{fish}$, as described herein.
Figure 6:
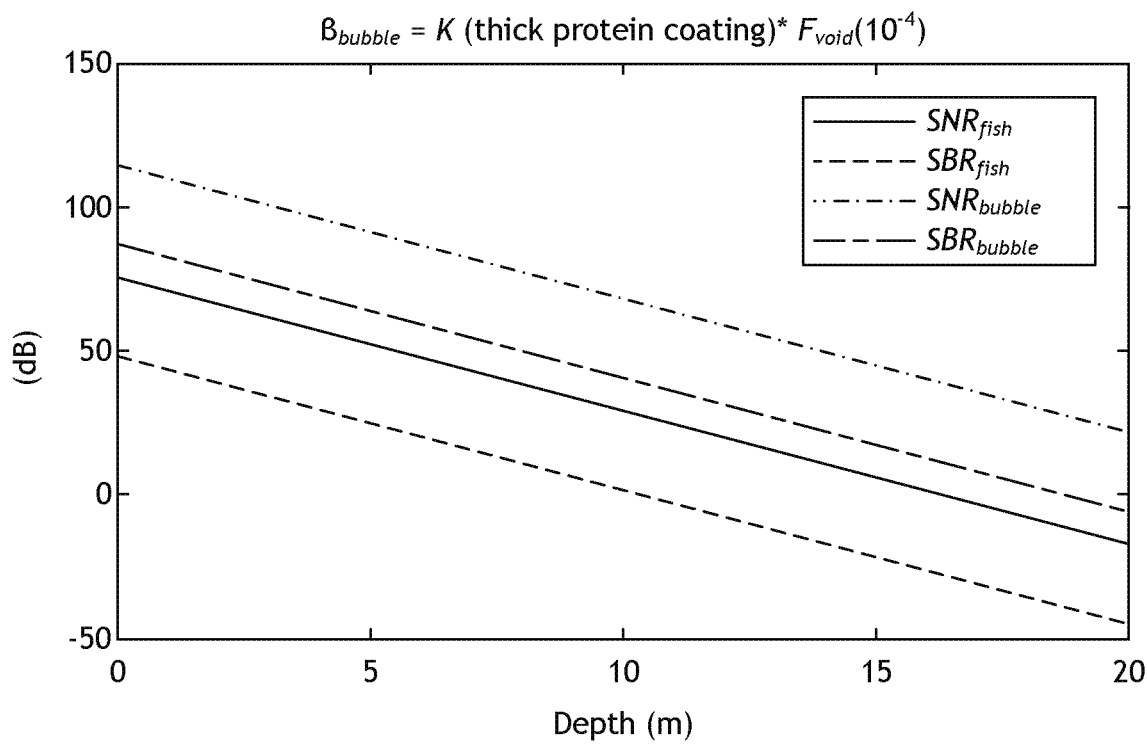
FIG. 6 is a plot showing signal-to-noise ratio and signal-to-background ratio for volume scattering coefficient $\beta_{bubble}$, with a thick protein coating and a void fraction of bubbles beneath the LIDAR footprint of $10^{-4}$, compared to $\beta_{fish}$, as described herein.
Figure 7:
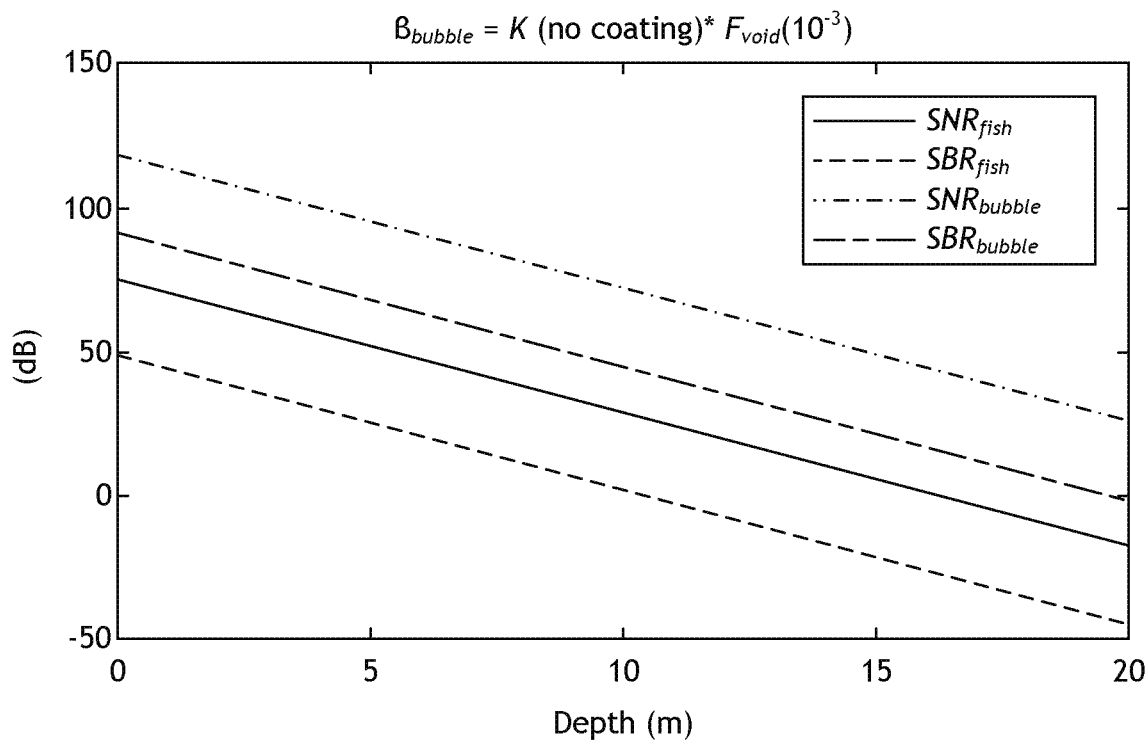
FIG. 7 is a plot showing signal-to-noise ratio and signal-to-background ratio for volume scattering coefficient $\beta_{bubble}$, with no coating and a void fraction of bubbles beneath the LIDAR footprint of $10^{-3}$, compared to $\beta_{fish}$, as described herein.
Figure 8:
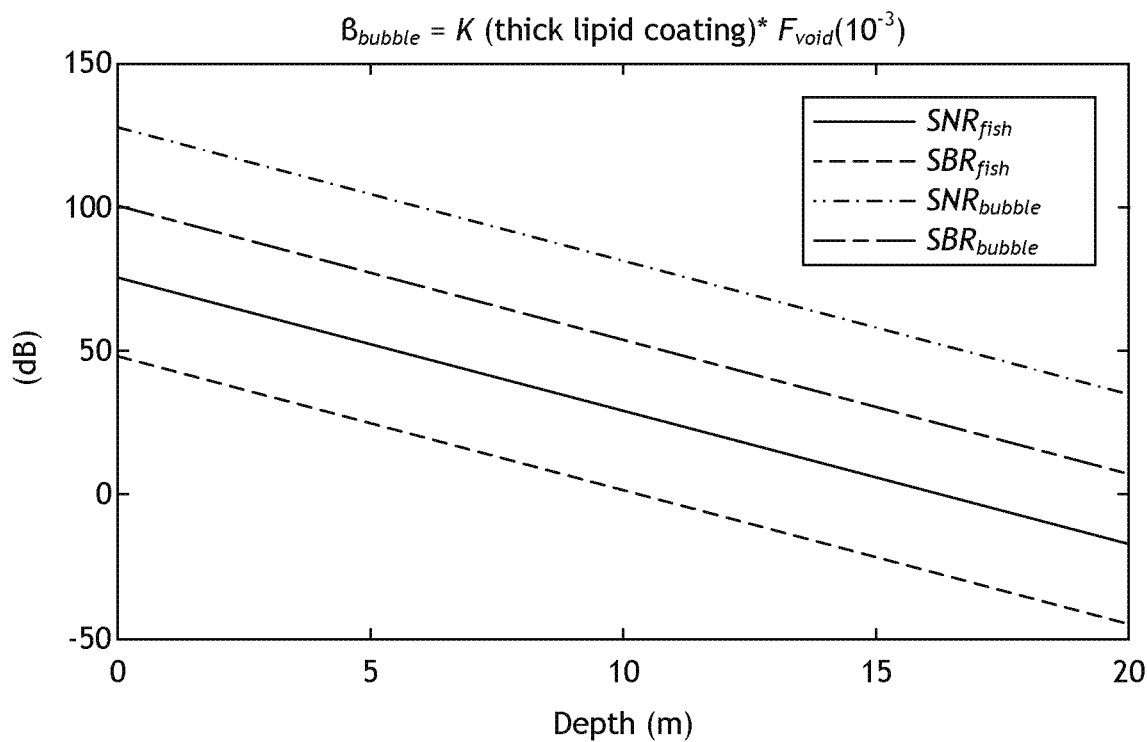
FIG. 8 is a plot showing signal-to-noise ratio and signal-to-background ratio for volume scattering coefficient $\beta_{bubble}$, with a thick lipid coating and a void fraction of bubbles beneath the LIDAR footprint of $10^{-3}$, compared to $\beta_{fish}$, as described herein.
Figure 9:
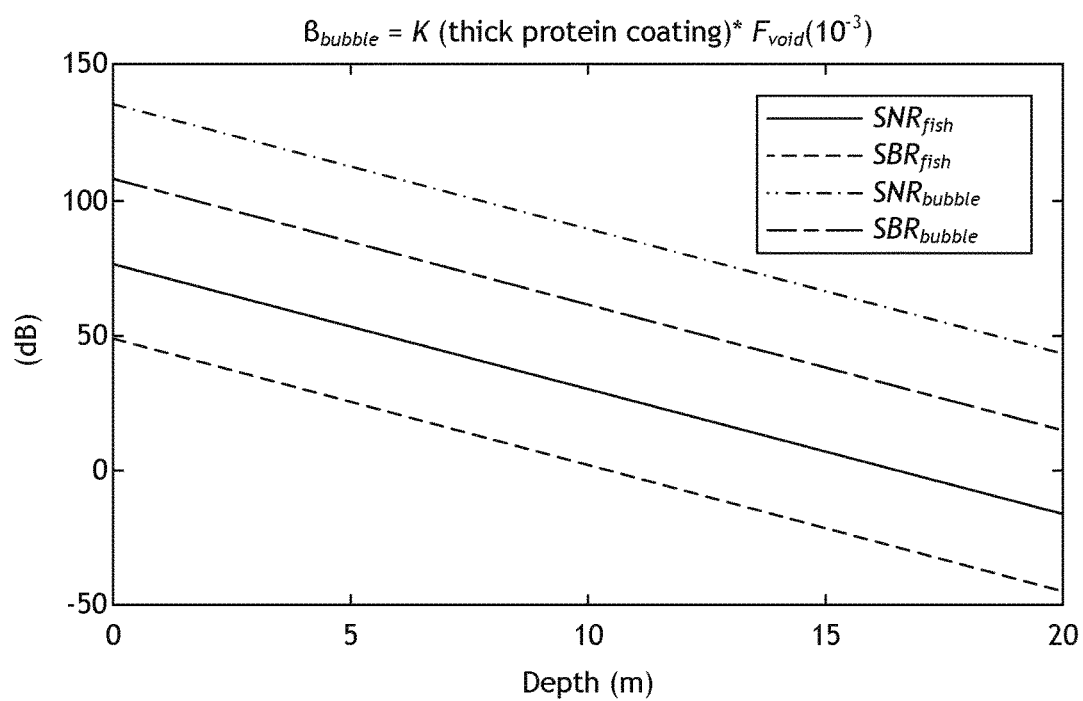
FIG. 9 is a plot showing signal-to-noise ratio and signal-to-background ratio for volume scattering coefficient $\beta_{bubble}$, with a thick protein coating and a void fraction of bubbles beneath the LIDAR footprint of $10^{-3}$, compared to $\beta_{fish}$, as described herein.

The present disclosure relates to the detection of hydrocarbon bubbles in water using Light Detection and Ranging (LIDAR). More particularly, the present disclosure relates to utilizing LIDAR to survey shallow water environments for the detection of surface hydrocarbon bubbles therein using LIDAR for the purposes of hydrocarbon exploration and/or brownfield remediation.

Unless otherwise indicated, all numbers expressing quantities of ingredients, properties such as molecular weight, reaction conditions, and so forth used in the present specification and associated claims are to be understood as being modified in all instances by the term "about." Accordingly, unless indicated to the contrary, the numerical parameters set forth in the following specification and attached claims are approximations that may vary depending upon the desired properties being sought by the embodiments of the present invention. At the very least, and not as an attempt to limit the application of the doctrine of equivalents to the scope of the claim, each numerical parameter should at least be construed in light of the number of reported significant digits and by applying ordinary rounding techniques.

One or more illustrative embodiments incorporating the invention embodiments disclosed herein are presented herein. Not all features of a physical implementation are described or shown in this application for the sake of clarity. It is understood that in the development of a physical embodiment incorporating the embodiments of the present invention, numerous implementation-specific decisions must be made to achieve the developer's goals, such as compliance with system-related, business-related, government-related and other constraints, which vary by implementation and from time to time. While a developer's efforts might be time-consuming, such efforts would be, nevertheless, a routine undertaking for those of ordinary skill in the art and having benefit of this disclosure.

While compositions and methods are described herein in terms of "comprising" various components or steps, the compositions and methods can also "consist essentially of" or "consist of" the various components and steps.

As used herein, the term "surface" with respect to the location of hydrocarbon bubbles in water refers to shallow depths of less than or equal to about 15 meters, or more preferably less than or equal to about 10 meters or less than about 5 meters (including 0 meters), encompassing any value and subset therebetween. Accordingly, "surface hydrocarbon bubbles" are located in shallow water depth environments, as defined above. These surface hydrocarbon bubbles may be detected for the purposes of hydrocarbon exploration and/or brownfield remediation. For hydrocarbon exploration, discovering surface hydrocarbon bubble plumes may be valuable in locating a hydrocarbon system (particularly a hydrocarbon system within the subsurface beneath the seafloor of the shallow water environments discussed above). The survey and/or discovery can aid in managing hydrocarbons (that is, one may manage hydrocarbons based at least in part upon a survey carried out as described herein) within the subsurface associated with the referenced shallow water environment. As used herein, "hydrocarbon management" or "managing hydrocarbons" includes any one or more of the following: hydrocarbon extraction; hydrocarbon production, (e.g., drilling a well and prospecting for, and/or producing, hydrocarbons using the well; and/or, causing a well to be drilled, e.g., to prospect for hydrocarbons); hydrocarbon exploration; identifying potential hydrocarbon systems such as those including hydrocarbon-bearing formations; determining candidate-sampling locations within a hydrocarbon system; evaluating a hydrocarbon system; characterizing a hydrocarbon system such as a hydrocarbon-bearing formation; identifying well locations; determining well injection rates; determining well extraction rates; identifying reservoir connectivity; acquiring, disposing of, and/or abandoning hydrocarbon resources; reviewing prior hydrocarbon management decisions; and any other hydrocarbon-related acts or activities, such activities typically taking place with respect to a hydrocarbon system and/or subsurface formation. The aforementioned broadly include not only the acts themselves (e.g., extraction, production, drilling a well, etc.), but also or instead the direction and/or causation of such acts (e.g., causing hydrocarbons to be extracted, causing hydrocarbons to be produced, causing a well to be drilled, causing the prospecting of hydrocarbons, etc.).

The method for surveying for and detecting, when present, surface hydrocarbon bubbles described herein is derived from known LIDAR models for detecting fish in freshwater ecosystems, as described in Roddewig et al., "Dual-polarization airborne lidar for freshwater fisheries management and research," Opt. Eng. 56(3), 031221 (2017), in combination with known theoretical bubble characteristics in view of LIDAR systems, as described in Churnside, "Lidar signature from bubbles in the sea," Opt. Express 18, 8294-8299 (2010).

The model of the present disclosure extends those known models to directly detect surface hydrocarbon bubbles using airborne LIDAR for the purposes of hydrocarbon exploration and/or brownfield remediation, which has been previously unexplored to the knowledge of the inventor. The LIDAR surveys shallow water environments of interest and, if present, can detect surface hydrocarbon bubbles; the LIDAR described according to the model of the present disclosure may be a non-scanning or scanning LIDAR system.

The known model for detecting fish in freshwater ecosystems utilized signal-to-noise ratio (SNR) and signal-to-background ratio (SBR) for detecting fish in freshwater ecosystems, and the received electrical LIDAR signal power, $Pf_{ish}(z)$, in watts at depth z was determined using Equation 1 below.

$$P_{fish}(z) = \left[\frac{E_0 A T_s^2 \eta n v}{2(nH+z)^2} \beta_{fish} e^{-2\alpha z}\right]^2 R_L, \quad \text{Equation 1}$$

where H is the altitude of the LIDAR, $\beta_{fish}$ is the volume scattering coefficient of fish at angle pi radians (assumed to be constant over depth), and z is water depth. The remaining parameters pertain to a particular LIDAR system and constants related to water clarity and light behavior. Such parameters include $E_o$, LIDAR laser pulse energy; A, LIDAR receiver aperture area; $T_s$, surface transmission; 11, LIDAR photomultiplier tube responsivity; n, index of refraction of water; v, speed of light in a vacuum; and a, LIDAR attenuation coefficient.

Using Equation 1, $SNR_{fish}$ and $SNR_{fish}$, each in decibels, for the LIDAR system of Equation 1 was determined, as shown in Equation 2 and Equation 3, respectively.

$$SNR_{fish} = 10 \cdot \log_{10}\left(\frac{P_{fish}}{P_{shot\ noise} + P_{quantization\ noise}}\right), \quad \text{Equation 2}$$

where $P_{shot\ noise}$ is the LIDAR shot noise based on elementary charge, output current of the photomultiplier tube, system bandwidth, and load resistance; and $P_{quantization\ noise}$ is the LIDAR quantization noise based on digitizer voltage step size.

$$SBR_{fish} = 10 \cdot \log_{10}\left(\frac{P_{fish}}{P_{background} + P_{dark\ current}}\right), \quad \text{Equation 3}$$

where $P_{background}$ is the LIDAR background noise based on background radiance, receiver aperture area, receiver field of view solid angle, and filter bandwidth; and $P_{dark\ current}$ is the LIDAR dark current noise based on dark current and load resistance.

The known model provided above pertaining to detection of fish was manipulated and evaluated to determine whether a similar LIDAR system may be used to detect surface hydrocarbon bubbles, as is described hereinbelow. In evaluating the use of LIDAR as a viable technique for detecting surface hydrocarbon bubbles, particularly for purposes of hydrocarbon exploration and brownfield remediation, the relevant parameter of interest is the volume scattering coefficient (i.e., ($\beta_{fish}$ in Equation 1 for fish). As used herein, the term "volume scattering coefficient" refers to the backwards scattering cross-section per unit volume. This parameter is of importance because it is an attribute of an object's (e.g., a fish, a grain, a bubble, a ball, etc.) physical and chemical characteristics that is proportional to how much backscatter per cross-sectional area of the object per unit volume. It can, thus, be used to define the difference between detecting a fish (according to the known model described above) and detecting a plume of hydrocarbon bubbles in shallow water (according to the model of the instant disclosure). That is, the model for successfully detecting fish in shallow water may be adapted to detect hydrocarbon bubbles in shallow water by accounting for the difference in the applicable volume scattering coefficients of fish and hydrocarbon bubbles, as described in greater detail herein.

The volume scattering coefficient of a bubble is a constant that varies depending on the composition of a particular bubble (e.g., whether the bubble has an outer layer that is lipid-based or protein-based and the void fraction of bubbles beneath the LIDAR footprint. As used herein, the term "void fraction of bubbles beneath the LIDAR footprint" refers to the volume of gas in the bubbles per unit volume of water.

Accordingly, the volume scattering coefficient of a hydrocarbon bubble may be determined using Equation 4 below.

$$\beta_{bubble} = K F_{void} \qquad \text{Equation 4}$$

where K is a bubble constant of proportionality, which depends on particular bubble coating and thickness, and $F_{void}$ is the void fraction of bubbles beneath the LIDAR footprint. Example known values for K are provided in Table 1 below. Particular K values may be derived experimentally or theoretically, and may range from about 233 m$^{-1}$sr$^{-1}$ to about 1500 m$^{-1}$sr$^{-1}$, for example. K values may be higher than those listed in Table 1, as the value depends on the scattering object's physical properties.

TABLE 1

| Coating Type | K Value |
| --- | --- |
| None | 233 m$^{-1}$sr$^{-1}$ |
| Thin Layer (Lipid or Protein) | 233 m$^{-1}$sr$^{-1}$ |
| Thick Lipid Layer | 671 m$^{-1}$sr$^{-1}$ |
| Thick Protein Layer | 1445 m$^{-1}$sr$^{-1}$ |

The determination of the whether a bubble has a thin or thick coating was determined, as described in Churnside, "Lidar signature from bubbles in the sea," Opt. Express 18, 8294-8299 (2010), based on comparison to wavelength. That is, the thicker the organic coating (e.g., lipid or protein), the greater the amount of wavelength backscatter for LIDAR detection. Accordingly, "thin" coating layers were defined as much less than (<<) a wavelength, and "thick" coating layers were defined as much greater than (>>) a wavelength such that phase difference is randomly distributed between 0 and 2π. The "thin" coating was not deemed to be discernable from a bubble having no coating.

Alternatively, and in view of Equation 1, the volume scattering coefficient of a hydrocarbon bubble may be expressed as shown in Equation 5 below.

$$\beta_{bubble} = C * \beta_{fish} \qquad \text{Equation 5}$$

where C is a constant representing the value necessary to convert the volume scattering coefficient of fish at angle pi radians to the volume scattering coefficient of hydrocarbon bubbles at angle pi radians. For example, a known volume scattering coefficient for fish, which was used in deploying a literal fish-detecting LIDAR system for detecting lake trout according to Equations 1-3, is 0.0016 m$^{-1}$sr$^{-1}$. This known volume scattering coefficient for fish may be multiplied by a constant factor to arrive at any one or more volume scattering coefficients for hydrocarbon bubbles.

Therefore, and with continued view to Equations 1-3, the received electrical LIDAR signal power ($P_{bubble}$), in watts at depth z, based on a modeled SNR ($SNR_{bubble}$) and SBR ($SBR_{bubble}$) for detecting hydrocarbon bubbles may be expressed as shown in Equations 6-8 below.

$$P_{bubble} = C^2 * P_{fish}(z) \qquad \text{Equation 6}$$

$$SNR_{bubble} = 10 \cdot \log_{10}\left(\frac{P_{bubble}}{P_{shot\ noise} + P_{quantization\ noise}}\right) \qquad \text{Equation 7}$$

$$SBR_{bubble} = 10 \cdot \log_{10}\left(\frac{P_{bubble}}{P_{background} + P_{dark\ current}}\right) \qquad \text{Equation 8}$$

Similarly, $SNRb_{bubble}$ and $SBRb_{bubble}$ may be written in terms of $SNRf_{fish}$ and $SBR_{fish}$ as shown in Equations 9 and 10 below.

$$SNR_{bubble} = SNR_{fish} 20\ \log_{10} C \qquad \text{Equation 9}$$

$$SNR_{bubble} = SNR_{fish} + 20\ \log_{10} C \qquad \text{Equation 10}$$

To detect hydrocarbon bubbles using the LIDAR model of the present disclosure (e.g., Equations 6-7), the $SNR_{bubble}$ must exceed zero (0) decibels and there must be separation (e.g., unequal) between the $SNR_{bubble}$ and the $SBR_{bubble}$. To achieve this result, an increase in receiver solid angle may be utilized to both increase the $SNR_{bubble}$ and depress the $SBR_{bubble}$. It is to be appreciated, however, that particular practical and safety limitations on the choice of receiver solid angle of the LIDAR system must be considered, such as to minimize increased unwanted background light to the LIDAR receiver, prevent laser light eye exposure to humans, and the like.

Additionally, LIDAR signals from hydrocarbon bubbles near a water's surface may be contaminated by the specular return through rough water surfaces, known as "glint return." Accordingly, to detect hydrocarbon bubbles in shallow waters, particularly those in a marine environment where the water surface may be comparatively rougher than other shallow water sources, the bubble volume scattering coefficient must be greater than the glint return.

As stated above, the volume scattering coefficient of hydrocarbon bubbles is based on coating type and thickness (constant K (Table 1)) and the void fraction of bubbles beneath the LIDAR footprint, $F_{void}$. The void fraction for use in the LIDAR model of the present disclosure may range from about 10$^{-8}$ to about 10$^{-3}$ for natural hydrocarbon seeps, encompassing any value and subset therebetween, with lower void fractions likely being undetectable and higher void fractions likely being even better detected, but less likely to exist in nature.

As noted previously, surveying a shallow water environment using the LIDAR system and techniques described herein can include detecting one or more hydrocarbon bubbles within the shallow water environment. Such surveys may be useful in brownfield remediation and/or hydrocarbon exploration. Hydrocarbon exploration as used herein may include hydrocarbon management, or managing hydrocarbons.

To facilitate a better understanding of the embodiments of the present disclosure, the following example of representative embodiments are given. In no way should the following example be read to limit, or to define, the scope of the invention.

Figure 10:
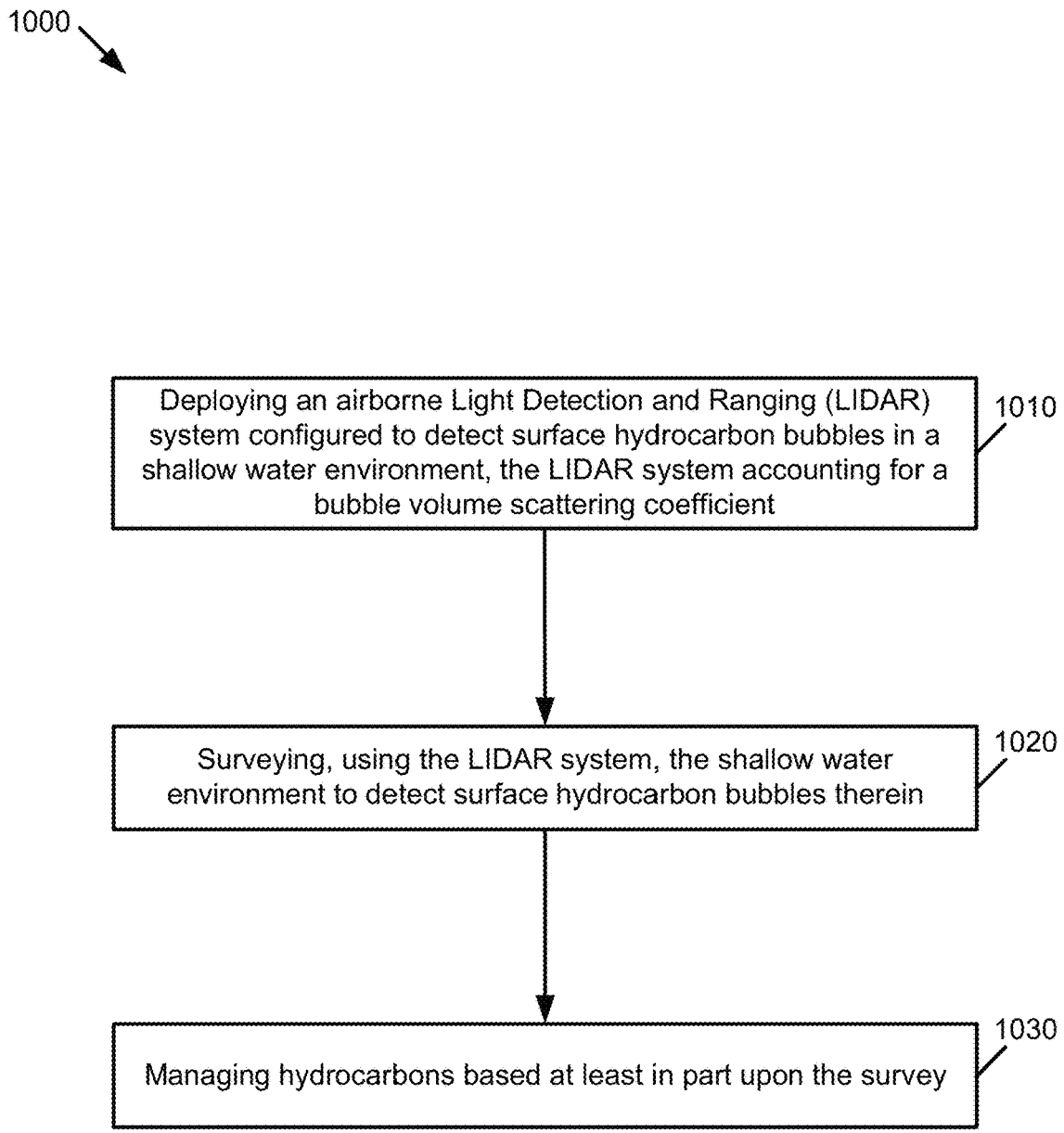
FIG. 10 is a flowchart.

FIG. 10 is a flowchart 1000. At 1010, an airborne Light Detection and Ranging (LIDAR) system configured to detect surface hydrocarbon bubbles in a shallow water environment is deployed, with the LIDAR system accounting for a bubble volume scattering coefficient. At 1020, surveying, using the LIDAR system, the shallow water environment to detect surface hydrocarbon bubbles therein is performed. At 1030, managing hydrocarbons is performed based at least in part upon the survey.

EXAMPLE

To evaluate the ability of the above-referenced LIDAR model for use in detecting surface hydrocarbon bubbles based on Equations 6-8 of the present disclosure, $SNR_{bubble}$ and $SBR_{bubble}$ were calculated based on various volume scattering coefficients for bubbles $\beta_{bubble}$), calculated according to Equation 4 of the present disclosure, using a combination of coating constants (K) and void fractions ($F_{void}$). The remaining parameters in Equations 6-8 remained constant and were based on known values for detecting fish, as described in Roddewig et al., "Dual-polarization airborne lidar for freshwater fisheries management and research," Opt. Eng. 56(3), 031221 (2017) and hereinabove.

The volume scattering coefficients used to calculate Pbubbte are provided in Table 2 below.

TABLE 2

| Sample No. | $\beta_{bubble}$ | K | $F_{void}$ (unitless) |
|---|---|---|---|
| 1 | 0.00233 $m^{-1}sr^{-1}$ | 233 $m^{-1}sr^{-1}$ | $10^{-5}$ |
| 2 | 0.0233 $m^{-1}sr^{-1}$ | 233 $m^{-1}sr^{-1}$ | $10^{-4}$ |
| 3 | 0.233 $m^{-1}sr^{-1}$ | 233 $m^{-1}sr^{-1}$ | $10^{-3}$ |
| 4 | 0.00671 $m^{-1}sr^{-1}$ | 671 $m^{-1}sr^{-1}$ | $10^{-5}$ |
| 5 | 0.0671 $m^{-1}sr^{-1}$ | 671 $m^{-1}sr^{-1}$ | $10^{-4}$ |
| 6 | 0.671 $m^{-1}sr^{-1}$ | 671 $m^{-1}sr^{-1}$ | $10^{-3}$ |
| 7 | 0.01445 $m^{-1}sr^{-1}$ | 1445 $m^{-1}sr^{-1}$ | $10^{-5}$ |
| 8 | 0.1445 $m^{-1}sr^{-1}$ | 1445 $m^{-1}sr^{-1}$ | $10^{-4}$ |
| 9 | 1.445 $m^{-1}sr^{-1}$ | 1445 $m^{-1}sr^{-1}$ | $10^{-3}$ |

For comparison, the calculated $SNR_{bubble}$ and $SBR_{bubble}$ based on the model described herein for detecting surface hydrocarbon bubbles was compared to the $SNR_{fish}$ and $SBR_{fish}$ based on Equations 1-3 provided herein. The $SNR_{fish}$ and $SBR_{fish}$ were calculated based on a scattering coefficient for fish (($\beta_{fish}$) of 0.0016 $m^{-1}sr^{-1}$. Void fraction was not considered for fish because they are larger than a bubble. The void fraction represents this physical process occurring on an ensemble of bubbles instead of a singular bubble. A school of fish may be analogous to void fraction, but only a single fish was used in the model of the present disclosure given its size. A collection of bubbles must be present to observe with LIDAR. The remaining parameters in Equations 1-3 remained constant and were identical to those used to calculate SNRbubbie and SBRbubbie, as shown in Table 2.

FIGS. 1-9 of the present disclosure correspond to Sample Nos. 1-9 in Tables 2 and 3. As provided above, in order to detect hydrocarbon bubbles using the LIDAR model of the present disclosure, the $SNR_{bubble}$ must exceed zero (0) decibels and there must be separation between the SNR-$b_ubb_{le}$ and the SBR$b_u$bbi$_e$. As shown, in each of FIGS. 1-9, the $SNR_{bubble}$ exceeds zero (0) decibels at least in shallow, "surface" waters of less than about 10 meters depth, as defined herein. Indeed, in each instance, the $SNR_{bubble}$ exceeded zero (0) decibels at depths greater than 10 meters. Moreover, in each of FIGS. 1-9, there is separation between the $SNR_{bubble}$ and the $SBR_{bubble}$. As shown, as the void fraction increases, corresponding to an increase in the volume of bubbles present, the capability of LIDAR bubble detection also increases.

Similarly, the results shown in FIGS. 1-9 demonstrate that bubble coatings substantially increase the signal-to-noise ratio, and thus the capability of LIDAR bubble detection. However, even with no coatings, the fish LIDAR of Equations 1-3 would also be expected to detect bubbles at void fractions as low as $10^{-5}$ (i.e., detecting bubbles as fish). However, bubbles with coatings, as would be the case with hydrocarbon bubbles, are more readily detected by the LIDAR model described herein, thus demonstrating its effectiveness at hydrocarbon bubble detection. Moreover, the LIDAR detection model described herein would further be capable of detecting thinly coated hydrocarbon bubbles and/or non-hydrocarbon, non-coated bubbles.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present invention. The invention illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces.

The invention claimed is:

1. A method comprising:
   deploying an airborne Light Detection and Ranging (LIDAR) system configured to detect surface hydrocarbon bubbles from natural hydrocarbon seeps from beneath a seafloor in a shallow water environment, the LIDAR system accounting for a bubble volume scattering coefficient;

differentiating surface hydrocarbon bubbles from the natural hydrocarbon seeps from other bubbles by surveying, using the LIDAR system, the shallow water environment; and performing, based at least in part upon the surveying of the shallow water environment to detect the surface hydrocarbon bubbles from the natural hydrocarbon seeps from beneath the seafloor, well placement for hydrocarbon extraction from beneath the seafloor.

2. The method of claim 1, wherein the bubble volume scattering coefficient is calculated according to the equation:

$$\beta_{bubble}=KF_{void},$$

where $B_{bubble}$ is the bubble volume scattering coefficient, K a bubble constant of proportionality, and $F_{void}$ is a void fraction of bubbles beneath LIDAR footprint.

3. The method of claim 2, wherein K is in the range of about 233 m$^{-1}$ sr$^{-1}$ to about 1500 m$^{-1}$ sr$^{-1}$.

4. The method of claim 3, wherein K is 233 m$^{-1}$ sr$^{-1}$, 671 m$^{-1}$ sr$^{-1}$, or 1445 m$^{-1}$ sr$^{-1}$.

5. The method of claim 2, wherein the $F_{void}$ is in the range of about 10$^{-8}$ to 10$^{-3}$.

6. The method of claim 1, wherein the shallow water environment has a depth less than about 15 meters.

7. The method of claim 1, wherein the shallow water environment has a depth of less than about 10 meters.

8. The method of claim 1, wherein the shallow water environment has a depth of less than about 5 meters.

9. The method of claim 1, wherein the LIDAR system has a signal-to-noise ratio of greater than zero (0) decibels, or has a signal-to-backscatter ratio greater than zero (0) decibels.

10. The method of claim 1, wherein the LIDAR system has a signal-to-noise ratio in decibels and a signal-to-background ration in decibels, wherein the signal-to-noise ratio and the signal-to-background ratio are unequal.

11. The method of claim 1, wherein the surveying of the shallow water environment comprises discovering surface hydrocarbon bubble plumes in order to locate a hydrocarbon system.

12. The method of claim 1, wherein detecting the surface hydrocarbon bubbles from the natural hydrocarbon seeps is performed using a LIDAR model that uses a signal-to-noise ratio for the hydrocarbon bubbles ($SNR_{bubble}$) and signal-to-background ratio for the hydrocarbon bubbles ($SBR_{bubble}$);

wherein the $SNR_{bubble}$ exceeds zero (0) decibels; and wherein the $SNR_{bubble}$ and the $SBR_{bubble}$ are unequal.

13. The method of claim 2, wherein glint return results from LIDAR signals from the surface hydrocarbon bubbles being contaminated by specular return; and wherein the bubble volume scattering coefficient is greater than the glint return.

* * * * *